US010309879B2

(12) United States Patent
Chen et al.

(10) Patent No.: US 10,309,879 B2
(45) Date of Patent: Jun. 4, 2019

(54) EXPANSION MICROSCOPY

(71) Applicant: Massachusetts Institute of Technology, Cambridge, MA (US)

(72) Inventors: Fei Chen, Cambridge, MA (US); Paul Warren Tillberg, Cambridge, MA (US); Edward Stuart Boyden, Chestnut Hill, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/627,310

(22) Filed: Feb. 20, 2015

(65) Prior Publication Data

US 2016/0116384 A1    Apr. 28, 2016

Related U.S. Application Data

(60) Provisional application No. 61/943,045, filed on Feb. 21, 2014.

(51) Int. Cl.

| G01N 1/36 | (2006.01) |
| C12Q 1/68 | (2006.01) |
| G01N 1/30 | (2006.01) |
| G02B 21/00 | (2006.01) |
| C12Q 1/6841 | (2018.01) |

(52) U.S. Cl.
CPC ............. *G01N 1/36* (2013.01); *C12Q 1/6841* (2013.01); *G01N 1/30* (2013.01); *G02B 21/0072* (2013.01); *G01N 2001/364* (2013.01)

(58) Field of Classification Search
None
See application file for complete search history.

(56) References Cited

U.S. PATENT DOCUMENTS

| 6,107,081 A | 8/2000 | Feeback et al. |
| 6,287,870 B1 | 9/2001 | Wardlaw |
| 2002/0176880 A1* | 11/2002 | Cruise ................. A61K 9/0024 424/423 |
| 2005/0090016 A1* | 4/2005 | Rich .................... H01J 49/0418 436/173 |
| 2009/0191627 A1 | 7/2009 | Fadeev et al. |
| 2009/0241681 A1* | 10/2009 | Machauf .............. B81B 3/0021 73/777 |
| 2010/0041128 A1 | 2/2010 | Banes et al. |
| 2010/0068725 A1* | 3/2010 | Armbruster ............ G01N 33/82 435/7.1 |
| 2011/0070604 A1 | 3/2011 | Gimzewski et al. |
| 2011/0091922 A1 | 4/2011 | Krishnan et al. |
| 2013/0045503 A1 | 2/2013 | Miyawaki et al. |

FOREIGN PATENT DOCUMENTS

| JP | 2005291759 A | 10/2005 | |
| JP | 2009191125 | 8/2009 | |
| JP | 2014-005231 | 6/2012 | |
| WO | 2012142664 A1 | 10/2012 | |
| WO | WO 2014025392 A1 * | 2/2014 | ............... G01N 1/30 |

OTHER PUBLICATIONS

Van Vliet, et al., The Biomechanics Toolbox: Experimental Approaches for Living Cells and Biomolecules, Acta Materialia 51: pp. 5881-5905, Aug. 23, 2003, [online], retrieved from the Internet, Oct. 23, 2015.

* cited by examiner

*Primary Examiner* — Bao Thuy L Nguyen
*Assistant Examiner* — Ellen J Marcsisin
(74) *Attorney, Agent, or Firm* — Elmore Patent Law Group, P.C.; Joseph Zucchero; Carolyn Elmore

(57) ABSTRACT

The present invention relates to an enlarged sample of interest for microscopy and methods for enlarging a sample of interest and the optical imaging of a sample of interest with resolution better than the classical microscopy diffraction limit, by synthesizing a swellable polymer network within a sample, it can be physically expanded, resulting in physical magnification.

46 Claims, 10 Drawing Sheets

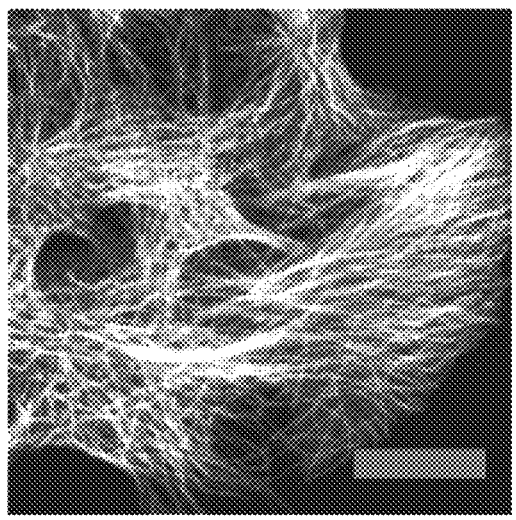
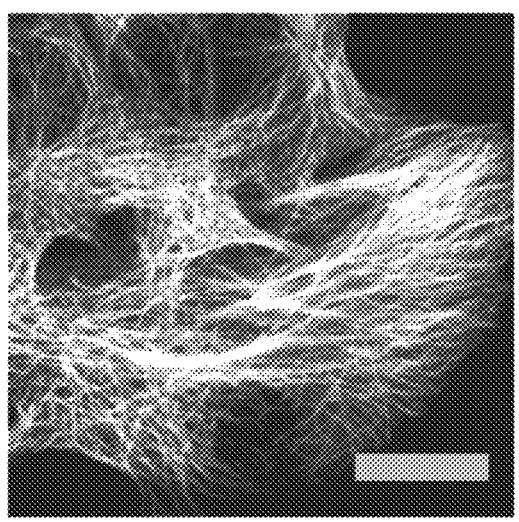
FIG. 5A  FIG. 5B
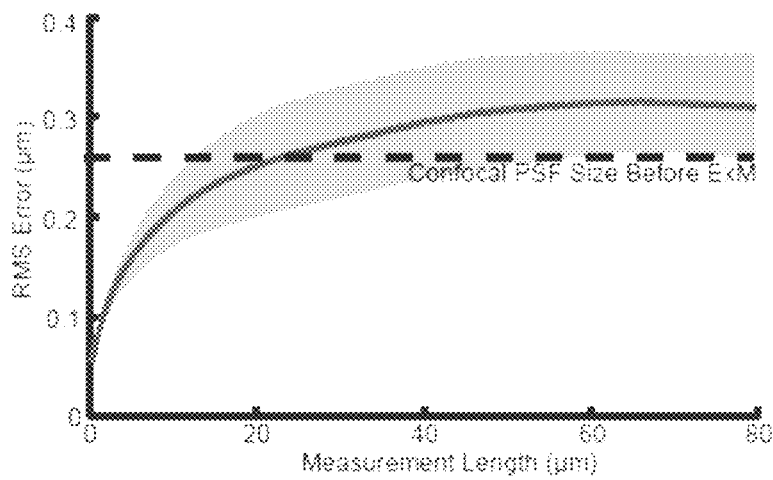
FIG. 5C
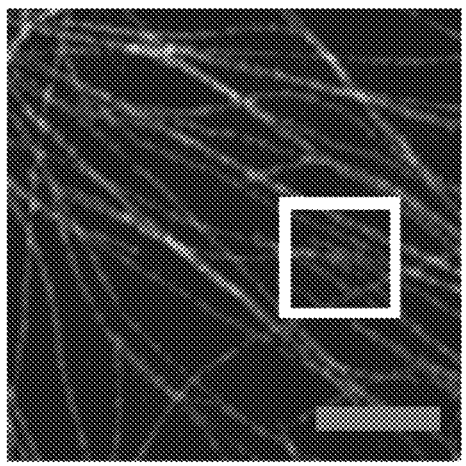
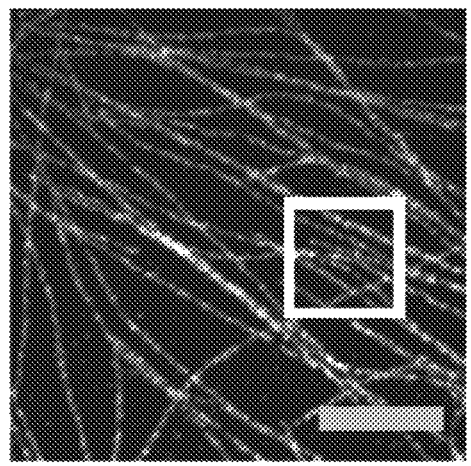
FIG. 5D  FIG. 5E

EXPANSION MICROSCOPY

RELATED APPLICATIONS

This application claims the benefit of U.S. provisional application Ser. No. 61/943,045, filed on Feb. 21, 2014, the contents of which are incorporated herein by reference in its entirety.

STATEMENT REGARDING FEDERALLY SPONSORED RESEARCH OR DEVELOPMENT

This invention was made with U.S. government support under Grant Number 1DP1NS087724, awarded by the National Institutes for Health. The government has certain rights in this invention.

FIELD OF THE TECHNOLOGY

The present invention relates to microscopy and, in particular, to optical imaging of biological specimens.

BACKGROUND

Microscopy has provided valuable biological information by optically magnifying images of small structures in fixed cells and tissues. However, the resolution of such imaging techniques are restricted to approximately half the wavelength of the illuminating source. In the visible region of the spectrum this is on the order of a quarter to a third of a micron (250-330 nm). Unfortunately, there is a vast range of biological structures/systems where non-invasive observations below this length scale are inaccessible to conventional optical microscopy.

There has been considerable activity aimed at developing optical techniques that reveal structure on the 100 nm length scale and below. For example, the development of super-resolution microscopy allowed for the visualization of a sample with resolution better than 250 nanometers and down to 20 nm. However, these techniques require specialized and demanding imaging conditions, specially designed fluorescent proteins, or expensive new machines and additional technical training to use the machines, and has difficulty with thick structures such as tissue sections or tumors.

Thus, there is a need for higher resolution microscopy that can work with current diffraction limited microscopes and can optically magnify larger samples, such as tissue sections or tumors, with nanoscale precision.

SUMMARY

The present invention is a method for optical imaging of biological specimens with resolution better than the classical microscopy diffraction limit, based on physically expanding the specimen itself. In this method, cultured cells, fixed tissue, or in principle other types of samples of interest, including biological materials, are infused with a composition, or chemical cocktail, that results in it becoming embedded in the sample material, and then the composition can be expanded isotropically, preferably with nanoscale precision, in three dimensions.

In an embodiment of this concept, the composition comprises a polyelectrolyte hydrogel (or the components thereof), which can swell macroscopically, for example, in low-salt water. The composition can comprise a tag or other feature of interest (for example, fluorescent dye molecules that have been delivered to the biological sample via antibody staining) which can be anchored (e.g., chemically) into the hydrogel before expansion. Following anchoring, the specimen is subjected to an enzymatic digestion (or other digestion) to disrupt the underlying network of biological molecules, leaving the tags of interest (e.g., the fluorescent dye molecules) intact and anchored to the gel. In this way, the mechanical properties of the gel-biomolecule hybrid material are rendered more spatially uniform, allowing isotropic expansion with minimal artifacts.

The swollen material with embedded biological specimen can be imaged on any optical microscope, allowing effective imaging of features below the classical diffraction limit. Since the resultant specimen can be transparent, custom microscopes capable of large volume, wide field of view, fast 3-D scanning may also be used in conjunction with the expanded sample.

This technology will enable new kinds of scientific exploration, such as mapping the brain, as well as new diagnostic, personalized medicine, histopathological, and other medical capabilities.

BRIEF DESCRIPTION OF THE DRAWINGS

Other aspects, advantages and novel features of the invention will become more apparent from the following detailed description of the invention when considered in conjunction with the accompanying drawings wherein:

FIG. 4A is a schematic of collapsed polyelectrolyte network (i), showing crosslinker (dot) and polymer chain (line), and expanded network (ii) after H2O dialysis. FIG. 4B is a photograph of fixed mouse brain slice. FIG. 4C is a photograph, post-ExM, of the sample (FIG. 4B) under side illumination. FIG. 4D is a schematic of a label that can be anchored to the gel at site of a biomolecule. FIG. 4E is a schematic of microtubules (green) and polymer network (orange). FIG. 4F shows the label of FIG. 4D hybridized to the oligo-bearing secondary antibody (gray) bound via the primary (gray) to microtubules (purple) and incorporated into the gel (orange lines) via the methacryloyl group (orange dot) and remains after proteolysis (dotted lines). Scale bars in FIGS. 4B and 4C are 5 mm. Schematics are not to scale.

FIGS. 5A through 5O show that expansion microscopy physically magnifies, with nanoscale isotropy. Images acquired via conventional microscopy (blue scale bars) vs. images acquired post-expansion (orange scale bars) were compared. FIG. 5A shows a confocal image of microtubules in HEK293 cells. FIG. 5B shows post-expansion confocal image of sample FIG. 5A. FIG. 5C depicts the root-mean-square (RMS) length measurement error of pre- vs. post-ExM confocal images of cultured cells (blue line, mean; shaded area, standard deviation; n=4 samples). FIG. 5D is a super-resolution structured-illumination microscopy (SR-SIM) image of microtubules. FIG. 5E shows post-expansion confocal image of the sample of FIG. 5D.

5F and FIG. 5G. FIG. 5O is a scatterplot of radii of CCPs measured via ExM vs. SR-SIM (n=50 CCPs from 3 samples). Green line, y=x line; shaded green region, half-pixel width of digitization error about the y=x line. Scale bars for pre- vs. post-ExM images: FIG. 5A 20 μm, FIG. 5B 20 μm (physical size post-expansion, 81.6 μm); FIG. 5D 2 μm, FIG. 5E 2 μm (9.1 μm); FIG. 5F 500 nm, FIG. 5G 500 nm (2.27 μm); FIG. 5K 2 μm, FIG. 5L 2 μm (8.82 μm); FIG. 5M 100 nm, FIG. 5N 100 nm (441 nm).

FIG. 6A is a wide field image of Thy1-YFP mouse brain slice showing fluorescence (white). FIG. 6B is a Post-expansion widefield image of sample FIG. 6A. FIG. 6C is the root-mean-square (RMS) length measurement error for pre- vs. post-ExM images of brain slices (blue line, mean; shaded area, standard deviation; n=4 samples). FIGS. 6D and 6E depict confocal fluorescence images of boxed regions in FIGS. 6A and 6B respectively, stained with presynaptic (anti-Bassoon, blue) and post-synaptic (anti-Homer1, red) markers, in addition to anti-GFP (green), pre- FIG. 6D vs. post- FIG. 6E expansion. FIG. 6F and FIG. 6G provide details of boxed regions in FIGS. 6D and 6E. FIG. 6H show a single representative synapse highlighted in FIGS. 6G and 6I shows the staining intensity for Bassoon (blue) and Homer1 (red) of the sample of FIG. 6H along white box long axis. Dotted black lines, Gaussian fits. a.u., arbitrary units. FIG. 6J shows Bassoon-Homer1 separation (n=277 synapses from 4 cortical slices). Scale bars for pre vs. post-ExM images: FIG. 6A 500 μm, FIG. 6B 500 μm (physical size post-expansion 2.01 mm); FIG. 6D 5 μm, FIG. 6E 5 μm (20.1 μm); FIG. 6F 2.5 μm, FIG. 6G 2.5 μm (10.0 μm) and FIG. 6H 250 nm (1.00 μm).

FIG. 7A is a volume rendering of a portion of hippocampus showing neurons (expressing Thy1-YFP, shown in green) and synapses (marked with anti-Bassoon (blue) and anti-Homer1 (red)). FIG. 7B is a volume rendering of dendrites in CA1 stratum lacunosum moleculare (slm). FIG. 7C is a volume rendering of dendritic branch in CA1 slm.

FIG. 7D shows the mossy fiber bouton in hilus of the dentate gyrus. Panels (i-iii), selected z-slices. Scale bars: FIG. 7A 100 μm in each dimension; FIG. 7B 52.7 μm (x), 42.5 μm (y), and 35.2 μm (z); FIG. 7C 13.5 μm (x), 7.3 μm (y), and 2.8 μm (z); FIG. 7D (i-iii) 1 μm.

DETAILED DESCRIPTION

Figure 1:
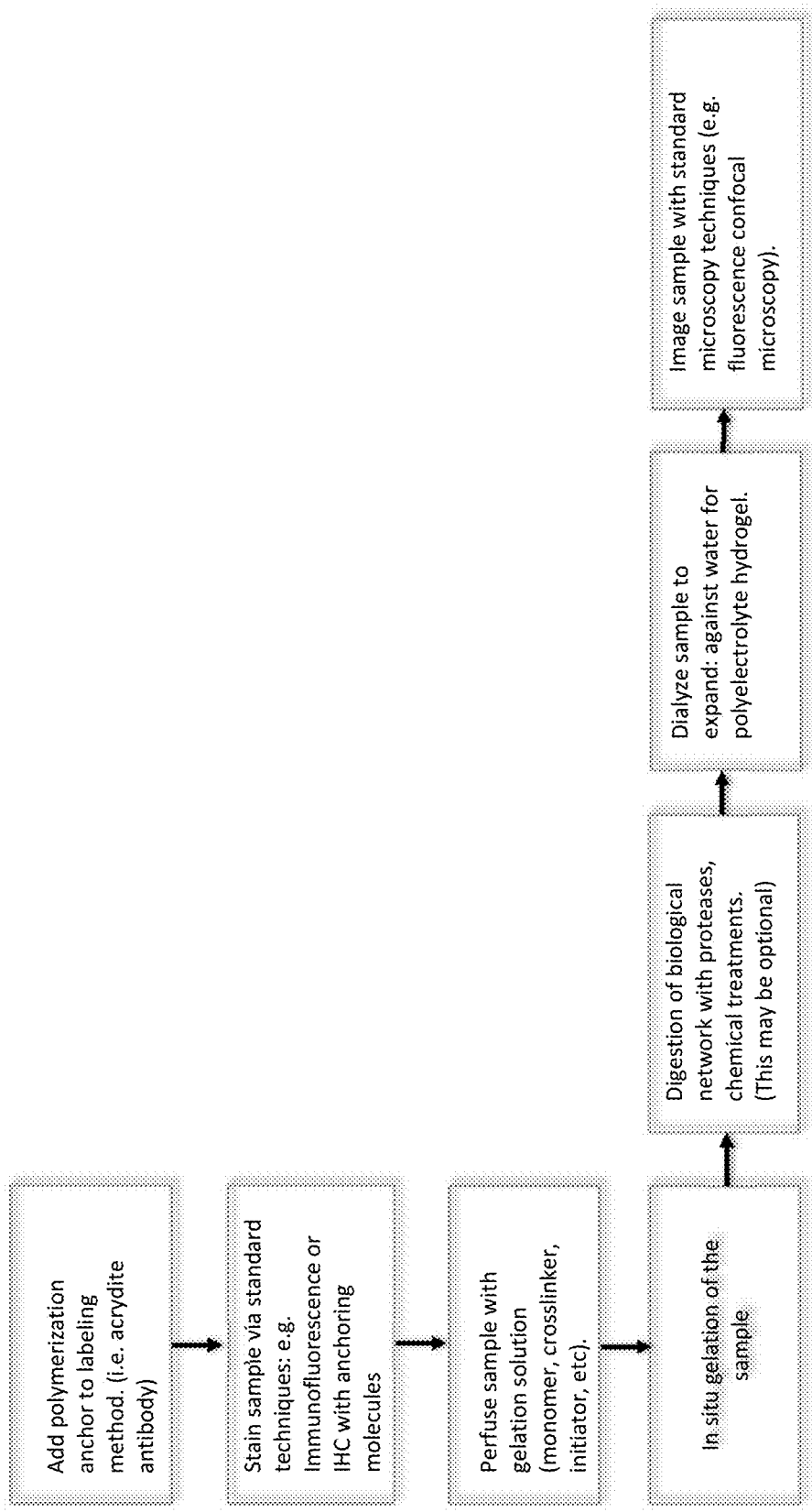
FIG. 1 is a flowchart depicting steps in an exemplary embodiment of the method of the invention.

The present invention relates to an enlarged sample of interest for microscopy and methods for enlarging a sample of interest and the optical imaging of a sample of interest with resolution better than the classical microscopy diffraction limit, by synthesizing a swellable polymer network within a specimen, it can be physically expanded, resulting in physical magnification. The invention also includes the use of compositions described herein for enlarging a sample of interest.

In one aspect, the invention provides an expandable sample of interest for microscopy. The expandable sample of interest comprises a sample of interest embedded in a swellable material. In certain embodiments, the sample of interest is labeled.

In a second aspect, the invention provides a method for enlarging a sample of interest for microscopy. The method comprises first embedding a sample of interest in a swellable material and then swelling the material. In certain embodiments, the sample of interest is labeled.

In a third aspect, the invention provides a method for preparing an enlargeable sample of interest for microscopy. In one embodiment, the method comprises embedding a sample of interest in a swellable material. In certain embodiments, the sample of interest is labeled.

In another aspect, the invention provides a microscopy method for producing a high-resolution image of a sample, the method comprising enlarging a sample of interest and viewing the enlarged sample under a microscope. In one embodiment, enlarging the sample of interest comprises embedding a sample of interest in a swellable material and then swelling the material. In certain embodiments, the sample of interest is labeled.

In a further aspect, the invention provides a method for the optical imaging of a sample of interest with resolution better than the classical microscopy diffraction limit, based on physically expanding the sample itself. In one embodiment, the method comprises embedding a sample of interest in a swellable material and then swelling the material. In certain embodiments, the sample of interest is labeled.

As used herein, the term "sample of interest" generally refers to, but not limited to, a biological, chemical or biochemical sample, such as a cell, array of cells, tumor, tissue, cell isolate, biochemical assembly, or a distribution of molecules suitable for microscopic analysis.

In a preferred embodiment, the sample of interest can be labeled or tagged. Typically, the label or tag will bind chemically (e.g., covalently, hydrogen bonding or ionic bonding) to the sample, or a component thereof. The tag can be selective for a specific target (e.g., a biomarker or class of molecule), as can be accomplished with an antibody or other target specific binder. The tag preferably comprises a visible component, as is typical of a dye or fluorescent molecule. Contacting the sample of interest with a label or tag results in a "labeled sample of interest." A fluorescently labeled sample of interest, for example, is a sample of interest labeled through techniques such as, but not limited to, immunofluorescence, immunohistochemical or immunocytochemical staining to assist in microscopic analysis. Thus, the label or tag is preferably chemically attached to the sample of interest, or a targeted component thereof. In a preferred embodiment, the label or tag, e.g. the antibody and/or fluorescent dye, further comprises a physical, biological, or chemical anchor or moiety that attaches or crosslinks the sample to the composition, hydrogel or other swellable material. The labeled sample may furthermore include more than one label. For example, each label can have a particular or distinguishable fluorescent property, e.g., distinguishable excitation and emission wavelengths. Further, each label can have a different target specific binder that is selective for a specific and distinguishable target in, or component of the sample.

As used herein, the term "swellable material" generally refers to a material that expands when contacted with a liquid, such as water or other solvent. Preferably, the swellable material uniformly expands in 3 dimensions. Additionally or alternatively, the material is transparent such that, upon expansion, light can pass through the sample. In one embodiment the swellable material is a swellable polymer or hydrogel. In one embodiment, the swellable material is formed in situ from precursors thereof. For example, one or more polymerizable materials, monomers or oligomers can be used, such as monomers selected from the group consisting of water soluble groups containing a polymerizable ethylenically unsaturated group. Monomers or oligomers can comprise one or more substituted or unsubstituted methacrylates, acrylates, acrylamides, methacrylamides, vinylalcohols, vinylamines, allylamines, allylalcohols, including divinylic crosslinkers thereof (e.g., N,N-alkylene bisacrylamides). Precursors can also comprise polymerization initiators and crosslinkers. In a preferred embodiment, the swellable polymer is polyacrylate and copolymers or crosslinked copolymers thereof. Alternatively or additionally, the swellable material can be formed in situ by chemically crosslinking water soluble oligomers or polymers. Thus, the invention envisions adding precursors (such as water soluble precursors) of the swellable material to the sample and rendering the precursors swellable in situ.

In an embodiment, embedding the sample in a swellable material comprises permeating (such as, perfusing, infusing, soaking, adding or other intermixing) the sample with the swellable material, preferably by adding precursors thereof. Alternatively or additionally, embedding the sample in a swellable material comprises permeating one or more monomers or other precursors throughout the sample and polymerizing and/or crosslinking the monomers or precursors to form the swellable material or polymer. In this manner the sample of interest is embedded in the swellable material.

Thus, a preferred embodiment of the invention a sample of interest, or a labeled sample, is permeated with a composition comprising water soluble precursors of a water swellable material and reacting the precursors to form the water swellable material in situ.

In certain embodiments, the sample of interest, or a labeled sample, can, optionally, be treated with a detergent prior to being contacted with the one or more swellable material precursors. The use of a detergent can improve the wettability of the sample or disrupt the sample to allow the one or more swellable monomer precursors to permeate throughout sample.

In a preferred embodiment, the sample is permeated with one or more monomers or a solution comprising one or more monomers or precursors which are then reacted to form a swellable polymer. For example, if the sample of interest is to be embedded in sodium polyacrylate, a solution comprising the monomers sodium acrylate and acrylamide, and the cross-linker N,N-methylenebisacrylamide are perfused throughout the sample. Once the sample, or labeled sample, is permeated, the solution is activated to form sodium polyacrylate. In a preferred embodiment, the solution comprising the monomers is aqueous. The solution is preferably at high concentration, such as about 50% or more saturation (defined herein as the percentage of solids present in the aqueous solvent in the same ratio as would result in precipitation under the conditions of permeation). The solution is preferably at high concentration, such as about 75% or more saturation, more preferably 90% or more saturation.

In a preferred embodiment, the sample (e.g., a labeled sample) is anchored or crosslinked to the swellable material before expansion. This can preferably be accomplished by chemically crosslinking a tag or label with the swellable material, such as during or after the polymerization or in situ formation of the swellable material. In an embodiment, after the labeled sample has been anchored to the swellable material, the sample is, optionally, subjected to a disruption of the endogenous biological molecules (or the physical structure of the sample of interest, where the sample is other than a biological material), leaving the tags or fluorescent dye molecules intact and anchored to the swellable material. In this way, the mechanical properties of the sample-swellable material complex are rendered more spatially uniform, allowing isotropic expansion with minimal artifacts.

As used herein, the "disruption of the endogenous biological molecules" of the sample of interest generally refers to the mechanical, physical, chemical, biochemical or, preferably, enzymatic digestion, disruption or break up of the sample so that it will not resist expansion. In an embodiment, a protease enzyme is used to homogenize the sample-swellable material complex. It is preferable that the disruption does not impact the structure of the swellable material but disrupts the structure of the sample. Thus, the sample disruption should be substantially inert to the swellable material. The degree of digestion can be sufficient to compromise the integrity of the mechanical structure of the sample or it can be complete to the extent that the sample-swellable material complex is rendered substantially free of the sample.

The sample-swellable material complex is then isoptropically expanded. Preferably, a solvent or liquid is added to the complex which is then absorbed by the swellable material and causes swelling. Where the swellable material is water swellable, an aqueous solution can be used.

In one embodiment, the addition of water allows for the embedded sample to expand 4× to 5× (e.g., 4.5×) or more its original size in 3-dimensions. Thus, the sample can be increased 100-fold or more in volume. This is because the polymer is embedded throughout the sample, therefore, as the polymer swells (grows) it expands the tissue as well. Thus, the tissue sample itself becomes bigger. Surprisingly, as the material swells isotropically, the anchored tags maintain their relative spacial relationship.

The swollen material with the embedded sample of interest can be imaged on any optical microscope, allowing effective imaging of features below the classical diffraction limit. Since the resultant specimen is preferably transparent, custom microscopes capable of large volume, wide field of view, 3-D scanning may also be used in conjunction with the expanded sample.

Examples

FIG. 1 is a flowchart depicting steps in an exemplary embodiment of the method of the invention.

Anchor-Able Dye System:

DNA sequences were ordered with 5' amine modification (Integrated DNA Technologies) and conjugated to secondary antibodies (Jackson ImmunoResearch) using a commercial kit (Solulink, Antibody-Oligonucleotide All-in-One Conjugation Kit). For the tertiary DNA/dye staining molecule, the complementary oligonucleotides are ordered with a 3' amine modification and a 5' Acrydite modification (Integrated DNA Technologies) and conjugated to dyes (Life Technologies and Sigma Aldrich) modified with NHS-ester chemistry per the manufacturer's directions. Conjugated DNA molecules were purified via reverse-phase HPLC, lyophilized and re-suspended in $ddH_2O$.

Cultured cells preparation and staining: All solutions are made up in 1×PBS, and incubations carried out at room temperature unless otherwise noted. HEK293-FT cells were fixed in 3% formaldehyde/0.1% glutaraldehyde (Electron Microscopy Sciences) for 10 minutes, followed by quenching in 100 mM glycine for 10 minutes and reduction with 0.1% NaBH4 for 7 minutes. Cells were permeabilized with 0.2% Triton for 15 minutes at room temperature and blocked with 5% normal donkey serum for one hour. Specimens were incubated with primary antibodies in blocking buffer at a concentration of 10 ug/mL for 1-4 hours, and then washed in PBS three times for 5 minutes each. Specimens were incubated with DNA-labeled secondary antibodies in DNA hybridization buffer (2×SSC buffer, 10% Dextran sulfate, 1 mg/mL yeast tRNA, 5% normal donkey serum) at a concentration of approximately 10 ug/mL for 1-4 hours, then washed in PBS as for primary. Specimens were incubated with dye-labeled DNA tertiaries in hybridization buffer at a concentration of 0.5 ng/uL overnight, then washed three times in 2×SSC.

Tissue Preparation and Staining:

Thy1-YFP-expressing mice were anesthetized with isoflurane and perfused transcardially with ice cold 4% paraformaldehyde. Brains were dissected out, left in 4% paraformaldehyde at 4° C. for one day, and then sunk in 30% sucrose with 100 mM glycine for one day. Tissue was frozen in −40° C. isopentane cooled with dry ice, embedded in M-1 embedding matrix (Thermo Scientific) and sliced on a cryotome. Slices were permeabilized and blocked in 1×PBS with 0.1% Triton and 2% normal donkey serum (slice blocking buffer) for at least six hours. Slices were incubated with primary antibodies in slice blocking buffer at a concentration of 10 ug/mL for 6-12 hours, and then washed in slice blocking buffer four times for thirty minutes each wash. Slices were incubated with DNA-labeled secondary antibodies in hybridization buffer at a concentration of approximately 10 ug/mL for 6-12 hours, then washed in slice blocking buffer as for primary. Specimens were incubated with dye-labeled DNA tertiaries in hybridization buffer at a concentration of 1 ng/uL for 6-12 hours, then washed in slice blocking buffer as for primary.

Hydrogel Embedding:

Monomer solution (1×PBS, 2M NaCl, 8.625% (w/w) sodium acrylate, 2.5% (w/w) acrylamide, 0.15% (w/w) N,N'-Methylenebisacrylamide is mixed fresh every week. Prior to embedding, monomer solution was cooled to 4° C. to prevent pre-mature gelation. Concentrated stocks (10% w/v) of ammonium persulfate (APS) initiator and tetramethylethylenediamine (TEMED) accelerator were added to the monomer solution up to 0.2% (w/w) each. Stained cells or tissue slices were incubated with the monomer solution plus APS/TEMED at 4° C. for two minutes (cultured cells) or ten minutes (slices), and then transferred to a 37° C. oven for one hour.

Digestion and Expansion:

Proteinase K (New England Biolabs) was diluted to 200 ug/mL in digestion buffer (50 mM Tris pH8, 1 mM EDTA, 0.5% Triton-X100, 1M NaCl, 0.8M guanidine HCl) and applied directly to gels in at least ten times volume excess. Gels can be formed in a Culturewell Chambered Coverglass (Invitrogen), and the chamber walls removed before adding digestion buffer in order to improve access of enzyme to the embedded tissue. The gels are then incubated in digestion buffer for greater than 6 hours to ensure complete digestion of all proteins. Digested gels were next placed in excess volume of doubly de-ionized or distilled water for several hours to expanded to ensure the gel reaches equilibrium. The expanded gel can be imaged on a standard optical microscope, though high light gathering and detector sensitivity are useful due to the volumetric dilution of bound dye molecules.

Imaging:

SIM imaging was performed on a Deltavision OMX SIM microscope. Stained cells were imaged within Culturewell Chambered Coverglass with SlowFade Gold antifade reagent (Invitrogen) for suppression of photobleaching and refractive index matching.

Post-expansion imaging was performed on a Perkin Elmer Spinning disk confocal or a Zeiss Laser Scanning Confocal (LSM 710). Briefly, expanded gels were placed in glass-bottom six well plates (In Vitro Scientific) and held in place with low-melting point agarose. Images were taken at with 1 Airy unit and Nyquist sampling on the LSM 710.

Figures 2A, 2B:
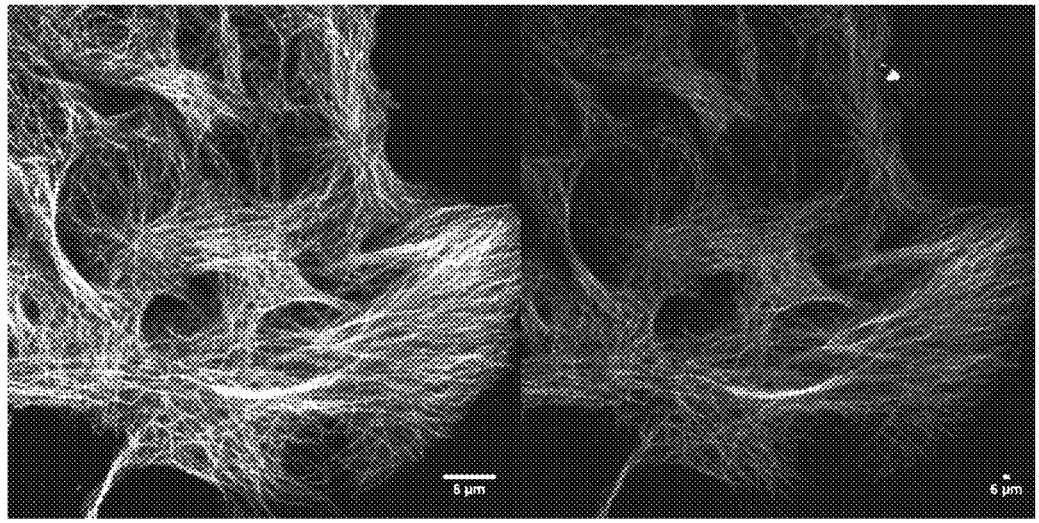
FIGS. 2A and 2B are examples using standard (FIG. 2A) and expansion microscopy according to the method of the invention (FIG. 2B).

FIGS. 2A-B present an example. FIG. 2A: Standard confocal image with 40×, 1.3 NA. FIG. 2B: Post-expansion with 20×, 0.8 NA. Scale bar: 5 µm. Note that magnification is being achieved in part by the physical expansion of the sample.

Figures 3A, 3B:
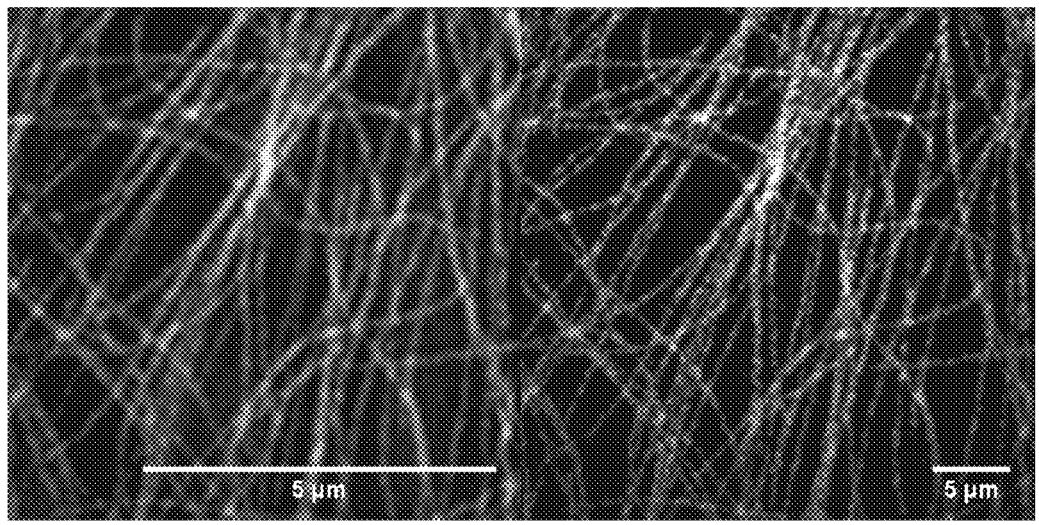
FIGS. 3A and 3B are further examples using standard (FIG. 3A) and expansion microscopy according to the method of the invention (FIG. 3B).

FIGS. 3A-B present an example. FIG. 3A: Structured Illumination Microscopy (Deltavision OMX), microtubules before expansion, 100×1.40 NA. FIG. 3B: Post Expansion 4.5× imaging on spinning disk confocal, 100×, 1.40 NA. Note that features smaller than the diffraction limit of light can be imaged on the confocal.

Expansion Microscopy (ExM). Any reference to color within the following description and corresponding figures can be found in Chen et al., *Science* (January 2015), Expansion Microscopy, v347(6221), pp. 543-548, which is incorporated herein by reference. However, the use of color is for illustrative purposes as the figures, and the textures therein, speak for themselves.

Figure 4B:
FIGS. 4A through 4F depicts Expansion microscopy (ExM) of the present invention.
Figure 4B:
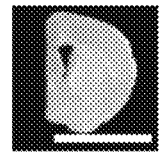
Figure 4A:
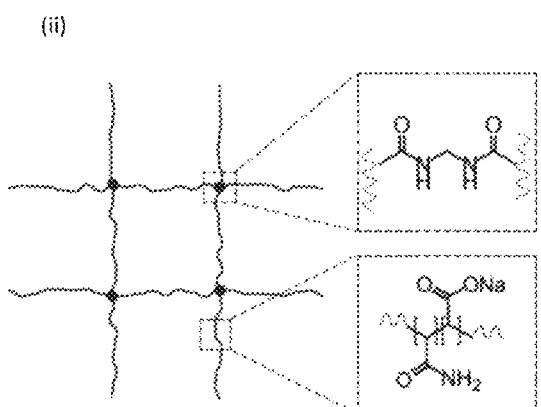
Figure 4C:
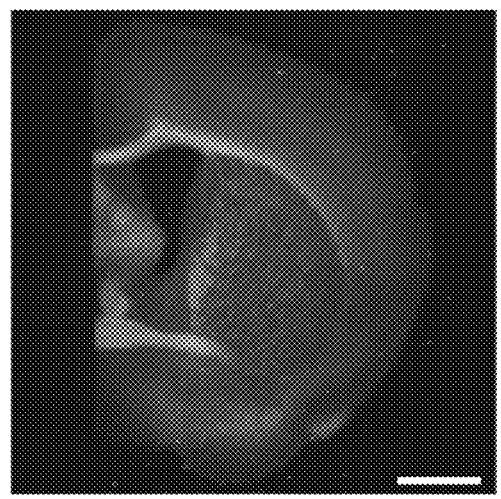
Figure 4D:

Sodium acrylate, a monomer used to produce super-absorbent materials, along with the co-monomer acrylamide and the crosslinker N—N'-methylenebisacrylamide were infused into chemically fixed and permeabilized brain tissue (FIG. 4B). After triggering free radical polymerization with ammonium persulfate (APS) initiator and tetramethylethylenediamine (TEMED) accelerator, the tissue-polymer composite was treated with protease to homogenize its mechanical characteristics. Following proteolysis, dialysis in water resulted in a 4.5-fold linear expansion, without distortion at the level of gross anatomy (FIG. 4C). Digestion was uniform throughout the slice. Expanded specimens were transparent as they consist largely of water. Thus, polyelectrolyte gel expansion is possible when the polymer is embedded throughout a biological sample.

Figure 4E:
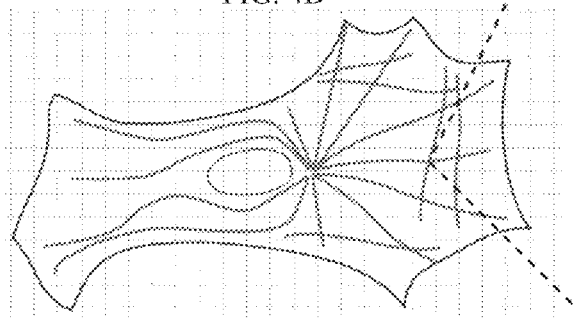
Figure 4F:
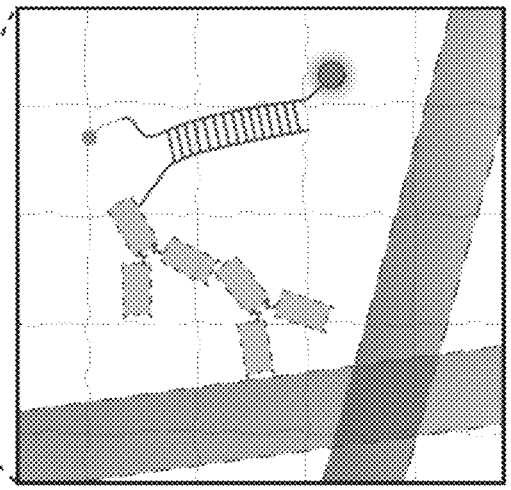

A fluorescent label, compatible with the proteolytic treatment and subsequent tissue expansion described herein, was incorporated directly into the polymer network. The label was tri-functional, comprising a methacryloyl group capable of participating in free radical polymerization, a chemical fluorophore for visualization, and an oligonucleotide that can hybridize to a complementary sequence attached to an affinity tag (e.g., a secondary antibody) (FIGS. 4E and F). Thus, the fluorescent tag is targeted to a bio-molecule of interest, yet remains anchored covalently with high yield to the polymer network.

Fluorescence imaging was performed using expansion microscopy (ExM) of the present invention, examining microtubules in fixed HEK293 cells labeled with the tri-functional label and imaged with confocal laser scanning micros-copy pre- vs. post-ExM processing. The post-E×M image (FIG. 5B) was registered to the pre-ExM image (FIG. 5A) via a similarity transformation resulting in visually indistinguishable images. To quantify the isotropy of ExM, the deformation vector field between the images via a non-rigid registration process was calculated. From this vector field, the root-mean-square error of feature measurements post-ExM was quantified. The errors in length were small (<1% of distance, for errors larger than the imaging system point spread function size) (FIG. 5C, n=4 samples).

Figure 5F:
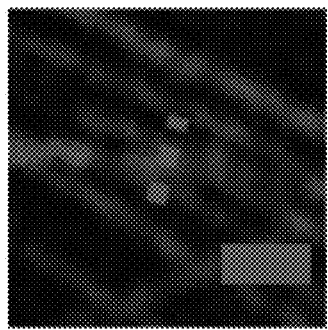
FIGS. 5F and 5G depict magnified views of boxed regions of FIG. 5D and FIG. 5E respectively.
Figure 5G:
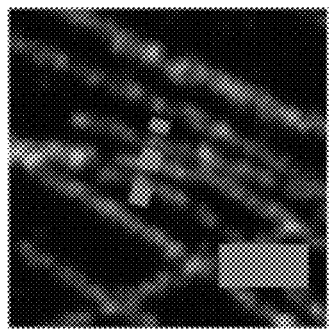
Figure 5H:
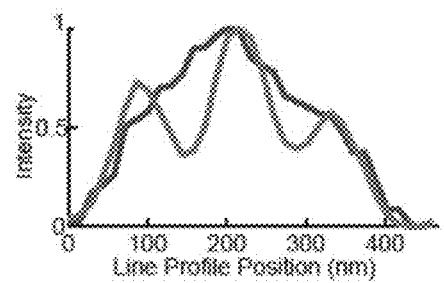
FIG. 5H depict profiles of microtubule intensity taken along the blue and orange dotted lines in FIG.
Figure 5I:
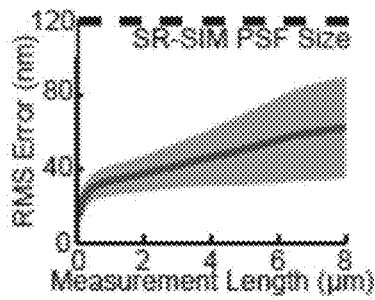
FIG. 5I shows RMS length measurement error of ExM vs. SR-SIM images (blue line, mean; shaded area, standard deviation; n=4 samples).
Figure 5J:
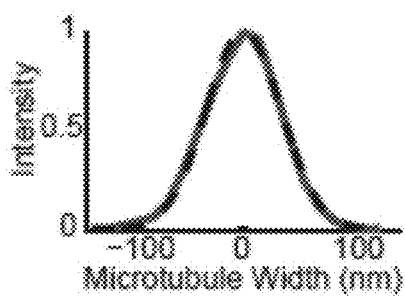
FIG. 5J depicts a transverse profile of a representative microtubule (blue line), with Gaussian fit (black dotted line).
Figure 5K:
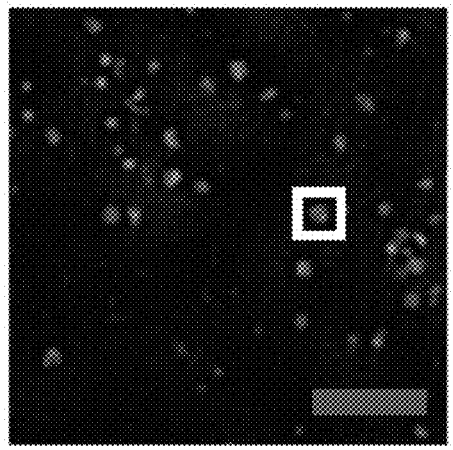
FIG. 5K is a SR-SIM image of clathrin coated pits (CCPs) in HEK293 cells.
Figure 5L:
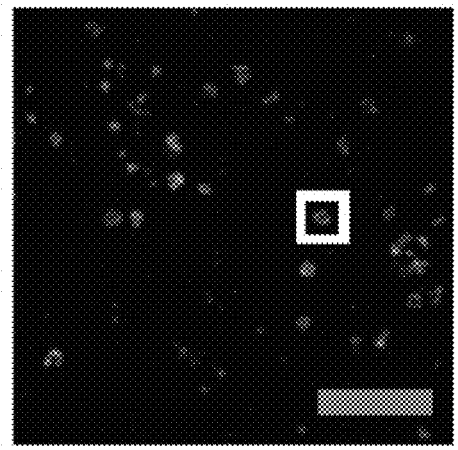
FIG. 5L is a post-expansion confocal image of the sample of FIG. 5K.
Figures 5M, 5N:
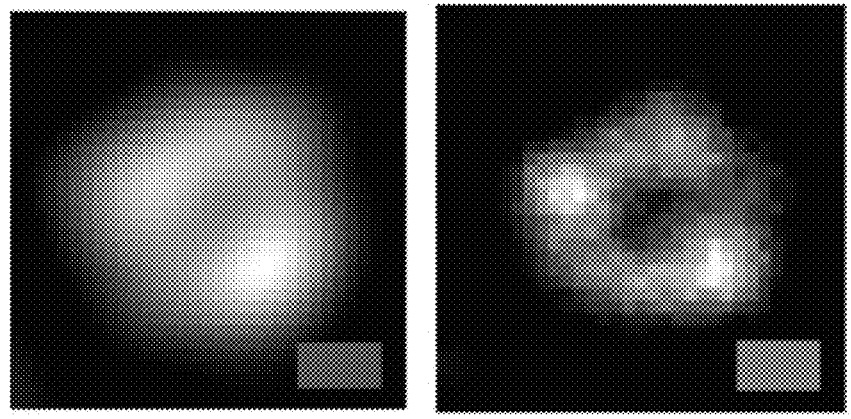
FIGS. 5M and 5N are magnified views of a single CCP in the boxed regions of FIG. 5K and FIG. 5L respectively.
Figure 5O:
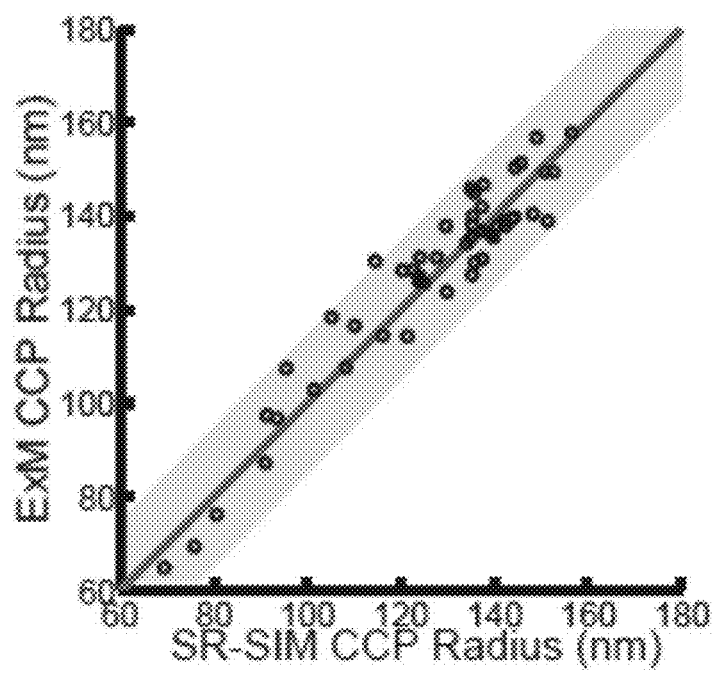

Pre-ExM conventional super-resolution images was compared to post-ExM confocal images. Features traditionally used to characterize the performance of super-resolution microscopes, including microtubules and clathrin coated pits were labeled and imaged with a super-resolution structured illumination microscope (SR-SIM) pre-ExM, and a spinning disk confocal post-ExM. Qualitatively (FIGS. 5, D and E), the images were similar, and quantitatively (FIG. 5I), measurement errors were again on the order of 1%, and well within the point spread function size of the SR-SIM microscope (n=4 samples). Microtubule networks were more sharply resolved in ExM (FIG. 5G) than with SR-SIM (FIG. 5F). ExM resolved individual microtubules that could not be distinguished with SR-SIM (FIG. 5H). Microtubules imaged with ExM presented a full-width at half-maximum (FWHM) (FIG. 5J) of 82.4±6.01 nm (mean±standard deviation, n=24 microtubules from 3 samples).

Clathrin coated pits were also well resolved (FIGS. 5, K and L). ExM resolved the central nulls of the pits better than SR-SIM (FIGS. 5, M and N). Clathrin-coated pit radii meas-ured via ExM and SR-SIM were highly correlated, with a slope of 1.001 (total least squares regression, confidence interval 0.013 with P<0.05, n=50 pits from 3 samples) (FIG. 5O). 49 of the 50 points lay within a half-pixel distance of the unity slope line, suggesting that variation in the ExM vs. SR-SIM comparison was within the digitization error of the measurement.

Figure 6A:
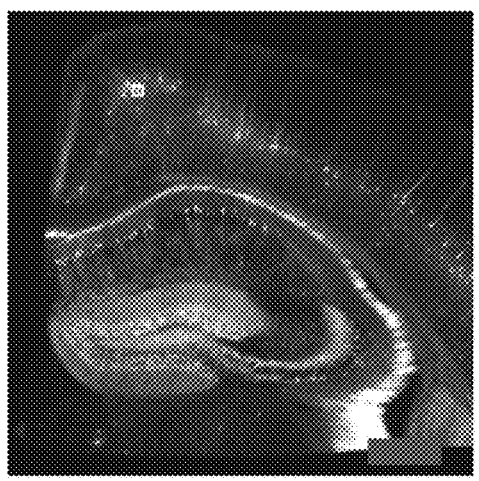
FIGS. 6A through 6J depict ExM imaging of mammalian brain tissue.
Figure 6B:
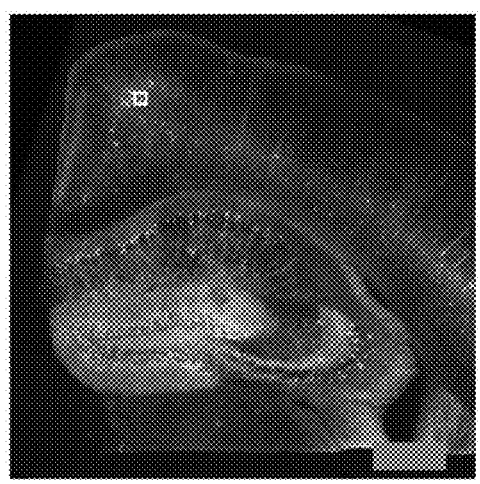
Figure 6C:
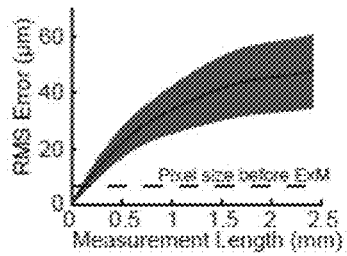

ExM was applied to fixed brain tissue. Slices of brain from Thy1-YFP-H mice expressing cytosolic YFP under the Thy1 promoter in a subset of neurons were stained with a tri-functional label bearing Alexa 488, using anti-GFP primary antibodies (which also bind YFP). Slices expanded ~4×, similar to the expansion factor in cultured cells. Pre- vs. post-ExM images taken on an epifluorescence microscope were compared. As with cultured cells, the post-ExM image (FIG. 6A) was registered to the pre-ExM image (FIG. 6B) via a similarity transformation. The registered images closely matched, although some features moved in or out of the depth of field, due to the axial expansion post-ExM. Quantitatively, post-ExM measurement errors (FIG. 6C, n=4 cortical slices) were 2-4%.

Figure 6D:
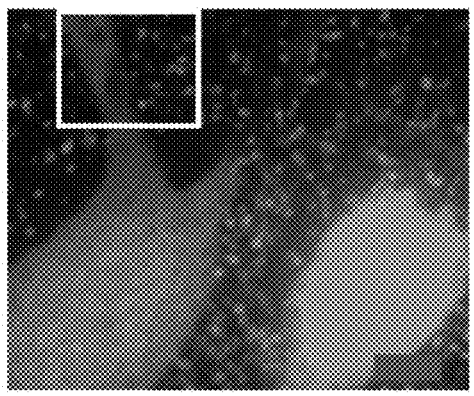
Figure 6E:
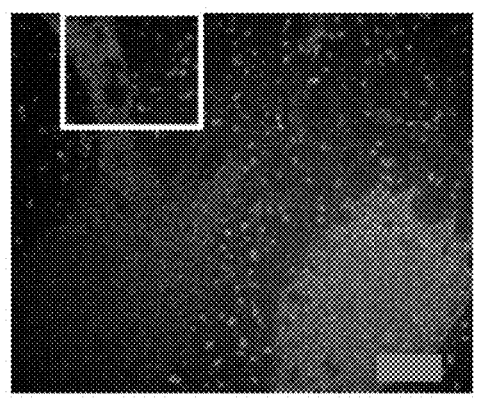
Figure 6F:
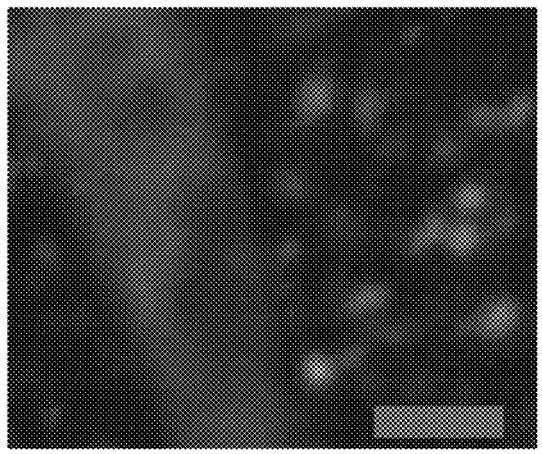
Figure 6G:
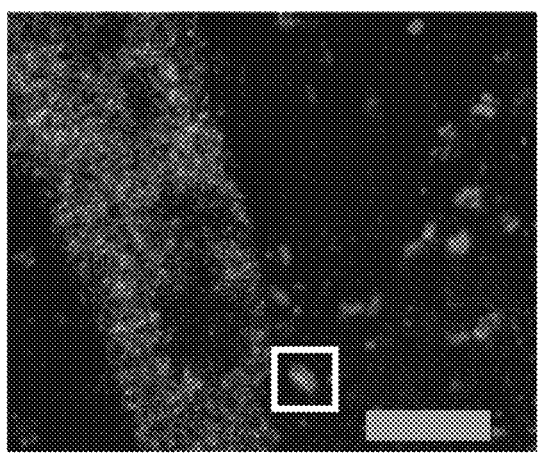
Figure 6H:
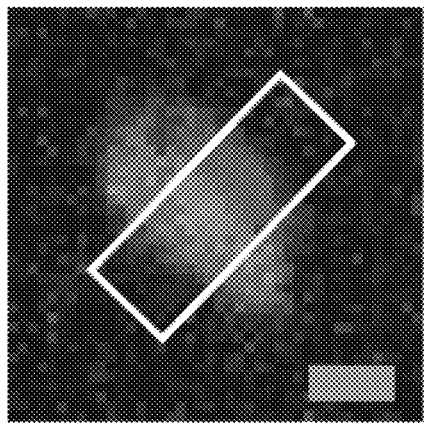
Figure 6I:
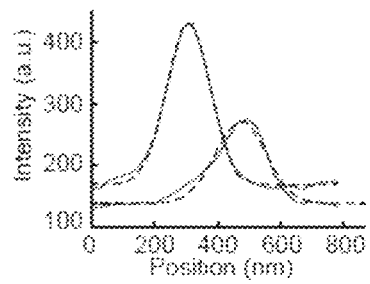
Figure 6J:
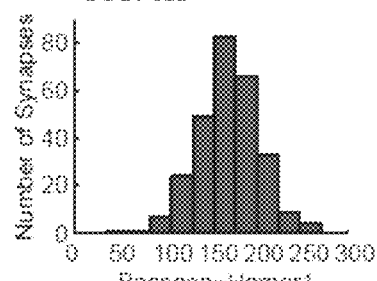

Tri-functional labels with different colors and oligonucleotides were synthesized to enable multicolor ExM. Pre- (FIG. 6D) vs. post-ExM (FIG. 6E) images of Thy1-YFP-H mouse cortex with ExM labels directed against YFP (green) and the pre- and post-synaptic scaffold-ing proteins Bassoon (blue) and Homer1 (red) were obtained. In the pre-ExM image, Bassoon and Homer1 staining form overlapping spots at each synapse (FIG. 6F), while the post-ExM image (FIG. 6G) shows clearly distinguishable pre- and post-synaptic labeling. The distance between the Bassoon and Homer1 scaffolds, as measured by ExM was quantified. The distributions of Bassoon and Homer1 staining intensity, taken along the line perpendicular to the synaptic cleft (FIG. 6H, boxed region), were fit to Gaussians (FIG. 6I). The Bassoon-Homer1 separation was 169±32.6 nm (FIG. 6J, n=277 synapses from 4 cortical slices).

Figure 7A:
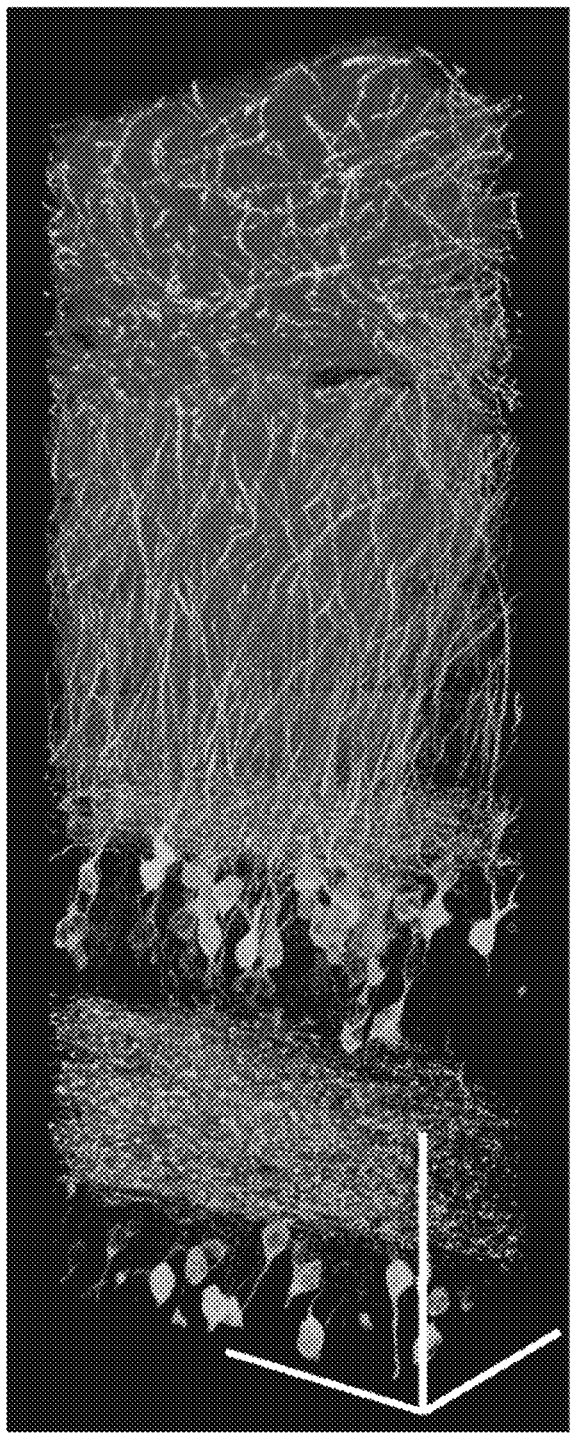
FIGS. 7A through 7D depicts scalable 3D super-resolution microscopy of mouse brain tissue.
Figure 7B:
Figure 7C:
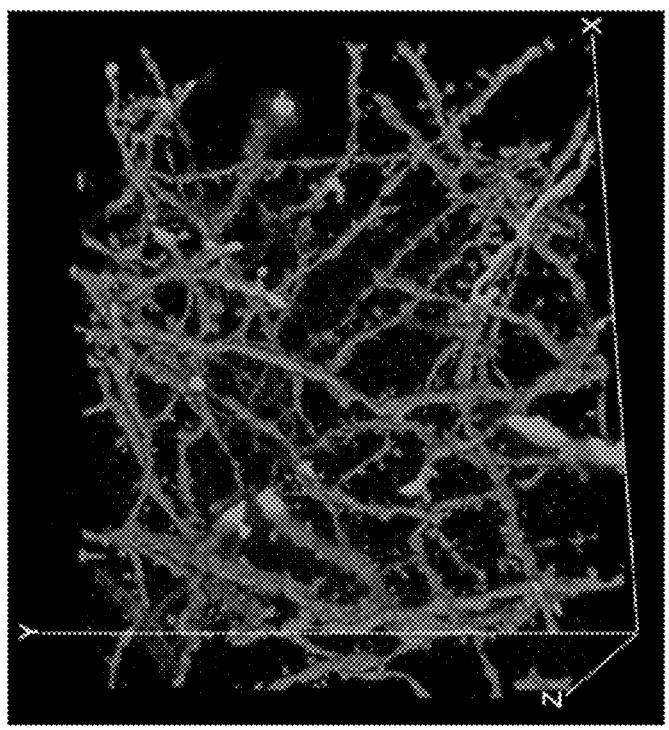
Figure 7D:
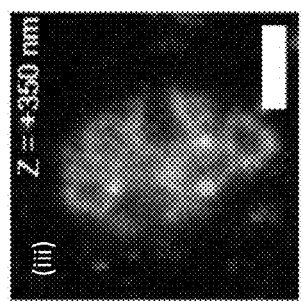
Figure 7D:

To explore whether expanded samples, scanned on fast diffraction-limited microscopes, could support scalable super-resolution imaging, a volume of the adult Thy1-YFP-H mouse brain spanning 500 µm×180 µm×100 µm (a typical slice thickness for immunohistochemistry) was imaged with three labels (FIG. 7A; anti-GFP, green; anti-Homer1, red; anti-Bassoon, blue). The diffraction limit of the confocal spinning disk microscope (with 40×, 1.15 NA, water immersion objective), divided by the expansion factor, yields an estimated effective resolution of ~70 nm laterally and ~200 nm axially. Shown in FIG. 7A is a 3D rendered image of the dataset. Zooming into the raw dataset, nanoscale features emerge (FIGS. 7B to D). A volume rendering of the YFP-expressing neurons in a subset of CA1 stratum lacunosum moleculare (slm) was performed, revealing spine morphology (FIG. 7B). Focusing on a dendrite in CA1 slm, the post-synaptic protein Homer1 was observed to be well localized to dendritic spine heads, with the presynaptic molecule Bassoon in apposition (FIG. 7C). Examination of a mossy fiber bouton in the hilus of the dentate gyrus reveals invaginations into the bouton by spiny excrescences of the opposing dendrite (FIG. 7D). Thus, ExM enables multiscale imaging and visualization of nanoscale features, across length scales relevant to understanding neural circuits.

While a preferred embodiment is disclosed, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention, which is not to be limited except by the claims that follow.

What is claimed is:

1. A method for enlarging a cell or solid tissue-sample, the method comprising:
   (a) labeling more than one biomolecule components of the sample with a trifunctional label, wherein the tri-functional label comprises an anchor capable of participating in polymerization and a visual label, further wherein the anchor is methacryloyl;
   (b) permeating the sample with a composition comprising sodium acrylate, acrylamide and N,N-methylenebisacrylamide;
   (c) polymerizing the composition within the sample to form a swellable material, wherein said polymerizing results in covalent crosslinking of the anchor to the swellable material to form a sample-swellable material complex; and
   (d) adding an aqueous solvent or liquid to cause the sample-swellable material complex to swell, thereby physically expanding the complex that results in an enlarged cell or tissue sample.

2. The method of claim 1, wherein the sample-swellable material complex is swelled isotropically when the aqueous solvent or liquid is added, thereby maintaining the relative spatial relationship of the labeled biomolecules.

3. The method of claim 1, wherein prior to performing the permeating step, the cell or tissue sample is treated with a detergent.

4. The method of claim 1, wherein prior to the step of adding the aqueous solvent or liquid to swell the sample-swellable material complex, the cell or tissue sample is subjected to digestion.

5. The method of claim 1, wherein the aqueous solvent or liquid is water.

6. A microscopy method for producing a high-resolution image of a cell or a tissue sample, the method comprising:

enlarging the sample by performing the method of claim 1; and
(ii) viewing the enlarged sample under a microscope.

7. The method of claim 6, wherein the sample-swellable material complex is swelled isotropically when the aqueous solvent or liquid is added, thereby maintaining the relative spatial relationship of the labeled biomolecules.

8. The method of claim 6, wherein prior to the permeating step, the cell or tissue sample is treated with a detergent.

9. The method of claim 6, wherein prior to the step of adding the aqueous solvent or liquid, the cell or tissue sample is subjected to digestion.

10. A method for optically imaging a cell or a tissue sample by physically enlarging the sample, the method comprising:
    (i) performing the method of claim 1, thereby achieving an enlarged cell or tissue sample; and
    (ii) optically imaging the enlarged cell or tissue sample by viewing the sample under a microscope.

11. The method of claim 10, wherein the sample-swellable material complex is swelled isotropically when the aqueous solvent or liquid is added, thereby maintaining the relative spatial relationship of the labeled biomolecules.

12. The method of claim 10, wherein prior to the step of permeating, the cell or tissue sample is treated with a detergent.

13. The method of claim 10, wherein prior to the step of adding the aqueous solvent or liquid, the cell or tissue sample is subjected to digestion.

14. A method for preparing an enlargeable cell or solid tissue sample, the method comprising:
    (a) labeling more than one biomolecule components of the sample with a trifunctional label, wherein the trifunctional label comprises an anchor capable of participating in polymerization and a visual label, further wherein the anchor is methacryloyl;
    (b) permeating the sample with a composition comprising sodium acrylate, acrylamide and N,N-methylenebisacrylamide;
    (c) polymerizing the composition within the sample to form a polyelectrolyte hydrogel, wherein said polymerizing results in covalent crosslinking of the anchor to the polyelectrolyte hydrogel to form a cell or a tissue sample-polyelectrolyte hydrogel complex, thereby resulting in a sample prepared to be enlarged.

15. The method of claim 14, wherein prior to the permeating step, the cell or tissue sample is treated with a detergent.

16. The method of claim 14, wherein prior to the step of adding the aqueous solvent or liquid to swell the sample-swellable material complex, the cell or tissue sample is subjected to digestion.

17. A method for isotropically enlarging a cell or solid tissue sample, the method comprising:
    (a) labeling more than one biomolecule components of the sample with a label, wherein the label comprises a biomolecule binding moiety and a polymerizable ethylenically unsaturated moiety;
    (b) permeating the sample with a composition comprising sodium acrylate, acrylamide and N,N-methylenebisacrylamide;
    (c) polymerizing the composition within the sample to form a swellable material, wherein said polymerizing results in covalent crosslinking of the polymerizable moiety to the swellable material to form a sample-swellable material complex; and
    (d) adding an aqueous solvent or liquid to cause the sample-swellable material complex to swell, thereby physically expanding the complex that results in an isotropically enlarged tissue sample.

18. The method of claim 17, wherein prior to performing the permeating step, the cell or tissue sample is treated with a detergent.

19. The method of claim 17, wherein prior to the step of adding the aqueous solvent or liquid to swell the sample-swellable material complex, the cell or tissue sample is subjected to digestion.

20. The method of claim 17, wherein the aqueous solvent or liquid is water.

21. The method of claim 17, further comprising the step of producing a high-resolution image of the sample by viewing the enlarged sample under a microscope.

22. The method of claim 17, further comprising the step of optically imaging the enlarged sample by viewing the sample under a microscope.

23. A method for isotropically enlarging a cell or solid tissue sample, the method comprising:
    (a) labeling more than one biomolecule components of the sample with a trifunctional label, wherein the trifunctional label comprises an anchor capable of participating in polymerization and a visual label, further wherein the anchor is methacryloyl;
    (b) permeating the sample with a composition comprising precursors of a crosslinked hydrogel comprising at least one polyelectrolyte monomer and a covalent crosslinker;
    (c) polymerizing the composition within the sample to form a swellable material, wherein said polymerizing results in covalent crosslinking of the anchor to the swellable material to form a sample-swellable material complex; and
    (d) adding an aqueous solvent or liquid to cause the sample-swellable material complex to swell, thereby physically expanding the complex that results in an isotropically enlarged tissue sample.

24. The method of claim 23, wherein prior to performing the permeating step, the cell or tissue sample is treated with a detergent.

25. The method of claim 23, wherein prior to the step of adding the aqueous solvent or liquid to swell the sample-swellable material complex, the cell or tissue sample is subjected to digestion.

26. The method of claim 23, wherein the aqueous solvent or liquid is water.

27. The method of claim 23, further comprising the step of producing a high-resolution image of the sample by viewing the enlarged sample under a microscope.

28. The method of claim 23, further comprising the step of optically imaging the enlarged sample by viewing the sample under a microscope.

29. A method for isotropically enlarging a cell or solid tissue sample, the method comprising:
    (a) contacting the sample with a tag comprising a binding moiety and a polymerizable moiety, wherein the tag binds a biomolecule component of the sample;
    (b) permeating the sample with a composition comprising precursors of a crosslinked hydrogel comprising at least one polyelectrolyte monomer and a covalent crosslinker;
    (c) polymerizing the composition within the sample to form a swellable material, wherein said polymerizing results in covalent crosslinking of the tag to the swellable material to form a sample-swellable material complex; and (d) adding an aqueous solvent or liquid to cause the sample-swellable material complex to swell, thereby physically expanding the complex that results in an isotropically enlarged tissue sample.

30. The method of claim 29, wherein prior to performing the permeating step, the cell or tissue sample is treated with a detergent.

31. The method of claim 29, wherein prior to the step of adding the aqueous solvent or liquid to swell the sample-swellable material complex, the cell or tissue sample is subjected to digestion.

32. The method of claim 29, wherein the aqueous solvent or liquid is water.

33. The method of claim 29, further comprising the step of producing a high-resolution image of the sample by viewing the enlarged sample under a microscope.

34. The method of claim 29, further comprising the step of optically imaging the enlarged sample by viewing the sample under a microscope.

35. A method for isotropically enlarging a cell or solid tissue sample, the method comprising:
   (a) contacting the sample with a tag comprising a binding moiety and a polymerizable moiety, wherein the tag binds a biomolecule component of the sample;
   (b) permeating the sample with a composition comprising precursors of a polyelectrolyte hydrogel comprising at least one polyelectrolyte monomer and a covalent crosslinker;
   (c) polymerizing the composition within the sample to form a polyelectrolyte hydrogel, wherein said polymerizing results in covalent crosslinking of the tag to the swellable material to form a sample- polyelectrolyte hydrogel complex; and
   (d) adding an aqueous solvent or liquid to cause the sample-polyelectrolyte hydrogel complex to swell, thereby physically expanding the complex that results in an isotropically enlarged tissue sample.

36. The method of claim 35, wherein prior to performing the permeating step, the cell or tissue sample is treated with a detergent.

37. The method of claim 35, wherein prior to the step of adding the aqueous solvent or liquid to swell the sample-swellable material complex, the cell or tissue sample is subjected to digestion.

38. The method of claim 35, wherein the aqueous solvent or liquid is water.

39. The method of claim 35, further comprising the step of producing a high-resolution image of the sample by viewing the enlarged sample under a microscope.

40. The method of claim 35, further comprising the step of optically imaging the enlarged sample by viewing the sample under a microscope.

41. A method for isotropically enlarging a cell or solid tissue sample, the method comprising:
   (a) contacting the sample with a tag comprising a binding moiety and an anchor, wherein the binding moiety binds to biomolecule components of the sample; wherein the anchor comprises a polymerizable moiety;
   (b) permeating the sample with a composition comprising at least one polyelectrolyte monomer and a covalent crosslinker;
   (c) initiating polymerization to form a hydrogel comprising the at least one polyelectrolyte monomer, covalent crosslinker and anchor, wherein the hydrogel is covalently bound to the biomolecule components of the sample to form a sample- hydrogel complex; and
   (d) adding an aqueous solvent or liquid to cause the sample-hydrogel complex to swell, thereby physically expanding the complex that results in an isotropically enlarged tissue sample.

42. The method of claim 41, wherein prior to performing the permeating step, the cell or tissue sample is treated with a detergent.

43. The method of claim 41, wherein prior to the step of adding the aqueous solvent or liquid to swell the sample-swellable material complex, the cell or tissue sample is subjected to digestion.

44. The method of claim 41, wherein the aqueous solvent or liquid is water.

45. The method of claim 41, further comprising the step of producing a high-resolution image of the sample by viewing the enlarged sample under a microscope.

46. The method of claim 41, further comprising the step of optically imaging the enlarged sample by viewing the sample under a microscope.

* * * * *

UNITED STATES PATENT AND TRADEMARK OFFICE
CERTIFICATE OF CORRECTION

PATENT NO. : 10,309,879 B2
APPLICATION NO. : 14/627310
DATED : June 4, 2019
INVENTOR(S) : Fei Chen, Paul Warren Tillberg and Edward Stuart Boyden Page 1 of 1

It is certified that error appears in the above-identified patent and that said Letters Patent is hereby corrected as shown below:

In the Claims

Column 12, Claim 17, Line 4:
After enlarged, delete "tissue".

Column 12, Claim 23, Line 41:
After enlarged, delete "tissue".

Column 13, Claim 29, Line 7:
After enlarged, delete "tissue".

Column 13, Claim 35, Line 42:
After enlarged, delete "tissue".

Column 14, Claim 41, Line 29:
After enlarged, delete "tissue".

Signed and Sealed this
Third Day of September, 2019

Andrei Iancu
*Director of the United States Patent and Trademark Office*